United States Patent [19]
Brade et al.

[11] Patent Number: 5,533,391
[45] Date of Patent: Jul. 9, 1996

[54] ELECTRIC RAIN SENSOR AND METHOD OF MANUFACTURING A SENSOR MEMBER THERETO

[75] Inventors: Claus B. Brade, Copenhagen; Niels Bartholin, Brøndby Strand, both of Denmark

[73] Assignee: V. Kann Rasmussen Industri A/S, Søborg, Denmark

[21] Appl. No.: 362,477

[22] PCT Filed: Jul. 9, 1993

[86] PCT No.: PCT/DK93/00222

§ 371 Date: Dec. 30, 1994

§ 102(e) Date: Dec. 30, 1994

[87] PCT Pub. No.: WO94/01649

PCT Pub. Date: Jan. 20, 1994

[30] Foreign Application Priority Data

Jul. 9, 1992 [DK] Denmark ............................. 0901/92

[51] Int. Cl.⁶ ...................... G01W 1/14; E05F 15/20
[52] U.S. Cl. .................... 73/170.19; 29/595; 29/849; 340/602; 49/357
[58] Field of Search ................... 73/170.19; 340/602; 29/595, 610.1, 620, 621, 829, 842, 848, 849; 338/34, 35; 200/61.05, 61.62; 52/200; 49/324, 357

[56] References Cited

U.S. PATENT DOCUMENTS

| 3,961,301 | 6/1976 | Fraioli | 338/35 |
| 4,264,902 | 4/1981 | Miller | 340/602 X |
| 4,578,995 | 4/1986 | Meyer | 73/170.17 |
| 4,665,351 | 5/1987 | Nyberg | 340/602 X |
| 4,837,986 | 6/1989 | Gagne | 52/200 X |
| 5,115,601 | 5/1992 | Yamaguchi et al. | 52/1 |

FOREIGN PATENT DOCUMENTS

| 368811 | 11/1982 | Austria . |
| 2363978 | 7/1975 | Germany . |
| 3246412 | 3/1988 | Germany . |
| 3939317 | 6/1990 | Germany . |
| 4023673 | 2/1992 | Germany . |
| 9103734 | 3/1991 | WIPO . |

*Primary Examiner*—Thomas P. Noland
*Attorney, Agent, or Firm*—Lane, Aitken & McCann

[57] ABSTRACT

An electrical rain sensor to be mounted on the outside of a main frame of an openable window, particularly a skylight, comprising a sensing element with two electrodes mounted opposite one another in an insulating holder, the distance between the electrodes being less than the size of a raindrop. To the electrodes an electric circuit is connected which by detection of a change in an electrical quantity caused by the presence of raindrops, activates a maneuvering device which closes the window. The holder (8) is produced by molding of an electrically insulating thermoplastic, wherein the supply lines to the electrodes (15, 16) as well as a heating element for the drying of the sensor are produced as inserts in the holder by molding of an electrically conductive thermoplastic polymer into excavated recesses and/or grooves in the holder (8). The electrodes can be designed as coatings of a weather resistant conducting material, particularly material containing graphite, the conducting material being applied to most of the surface of the sensor.

12 Claims, 3 Drawing Sheets

ELECTRIC RAIN SENSOR AND METHOD OF MANUFACTURING A SENSOR MEMBER THERETO

BACKGROUND OF THE INVENTION

The invention relates to an electric rain sensor for mounting on the outside of the main frame or on another stationary member of an openable window, in particular a skylight, of the type where opening and closing may be carried out by means of an electrical maneuvering device, said rain sensor comprising a sensing element with two electrodes opposite one another in or on a substantially plane sensing surface of an insulating holder, the distance between the electrodes being less than the size of a raindrop, means for applying a voltage between the electrodes and an electrical circuit connected to the electrodes for detecting a change in an electrical quantity caused by the presence of raindrops, a heating element being mounted on the holder for drying of the sensing surface, and the holder being produced by molding of an electrically insulating thermoplastic.

Such rain sensors are known for instance from DE-A-2363978, DE-A-4023673, and DE-A-3939317 in addition to CA-A-1119669 and are often installed in connection with electrically operated windows in order to ensure the closing of an open skylight in the event of rain or snow. In known installations the sensing element is frequently positioned inside on the main frame, in order to avoid exposure to bad weather resulting in contamination and corrosion to such a degree that the sensor no longer functions as intended. Positioning the sensing element on the inside, however, often results in a particular drawback, namely that it frequently is placed in such a manner—for instance on a vertical section of the main frame—as to be sheltered from the wind when the wind is in certain directions thereby being struck by the rain either too late or not at all.

DE-C-3 246 412 discloses a humidity sensing element for industrial application, wherein the electrodes are imbedded in an added insulating layer.

With some types of rain sensors a relatively long period of time may pass before the sensing surface—after having been exposed to rain—dries and consequently the window can only be opened after a significant time delay with respect to the end of the rainfall.

It has been attempted to avoid these problems by the positioning of a rain sensor of the kind mentioned above on the outside and attaching an electrical heating element to the sensor, the heating element being either permanently activated or turned on immediately after the sensor has become wet.

SUMMARY OF THE INVENTION

It is the object of the invention to provide an electric rain sensor to be mounted on the outside that avoids the mentioned drawback such that the risk of malfunction is reduced to a significant degree achieving in addition an even higher degree of safety against a malfunction caused by corrosion of electrodes, and furthermore a particularly robust and inexpensive design.

According to the invention this is achieved in that the heating element, and supply lines therefor and for the electrodes, are manufactured as inserts of the holder by molding of an electrically conducting thermoplastic polymer into excavated recesses and/or grooves in the holder.

In order to avoid the risk of desintegration of the exposed electrode sections at the sensor surface a preferred embodiment of the rain sensor is—according to the invention—characterized in that the electrodes comprise protective electrode coatings made from a weather resistant electrically conductive material on the sensor surface.

The invention furthermore relates to a method of manufacturing a sensing element for an electric rain sensor. According to the invention a simple and inexpensive manufacture of the sensing element is achieved by a method in which the jointly molded inserts of the electrodes and the heating element, in addition to their respective supply lines, are produced by molding an electrically conducting thermoplastic polymer into appropriately shaped excavated recesses and/or grooves in the holder.

BRIEF DESCRIPTION OF THE DRAWINGS

In the following the invention will be explained further with reference to the accompanying drawing, in which.

DETAILED DESCRIPTION OF THE PREFERRED EMBODIMENTS

Figure 1:
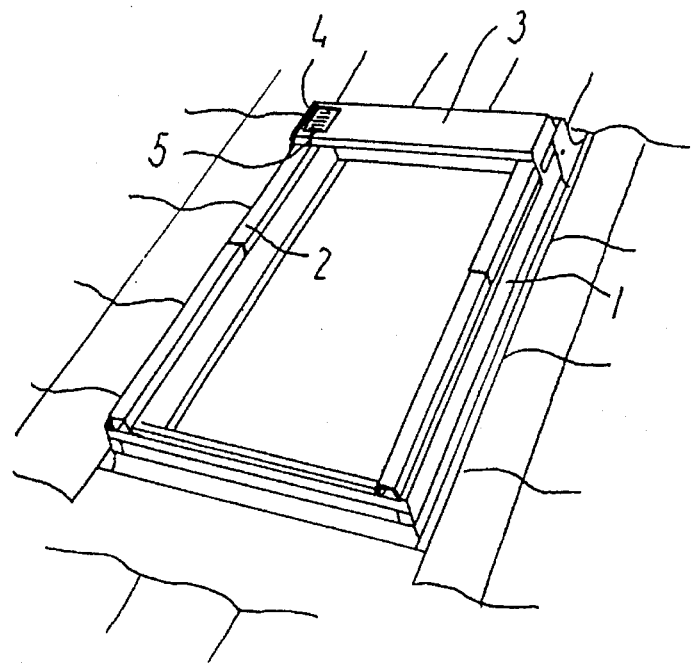
FIG. 1 shows an example of mounting of a rain sensor according to the invention onto a top-hinged skylight.

The skylight schematically illustrated in FIG. 1 comprises a main frame 1 and a top-hinged window frame 2. The opening and closing of the window may be performed in a known manner by means of an electrical maneuvering device comprising a motor unit mounted on the window frame and connected to an extendable arm. Such a maneuvering device can be operated from the inside, possibly by remote control, and may include a control circuit mounted on the main frame and including, for example, a microprocessor.

A sensing element 4 for a rain sensor according to the invention is mounted on a top cover 3, which is connected to the upper horizontal section of the main frame.

By means of a supply line 5 the sensing element 4 is connected to a sensing circuit which is a part of the control circuit 5 mentioned above.

Figure 2:
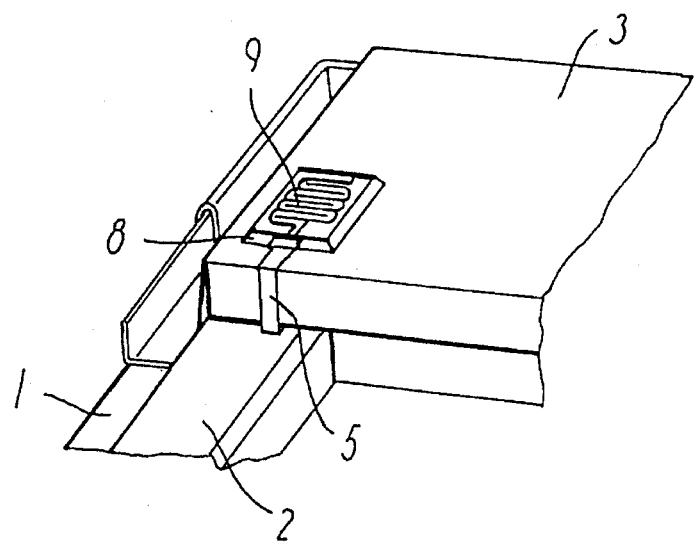
FIG. 2 the mounted sensor from FIG. 1 on a larger scale.

The sensing element 4 comprises—as further apparent from FIG. 2—a holder 8 with a top side 9 constituting the sensing surface of the element.

The holder 8 is preferably produced by injection molding of an electrically insulating thermoplastic, for instance polyamide, possibly with a fibreglass reinforcement.

Figure 3:
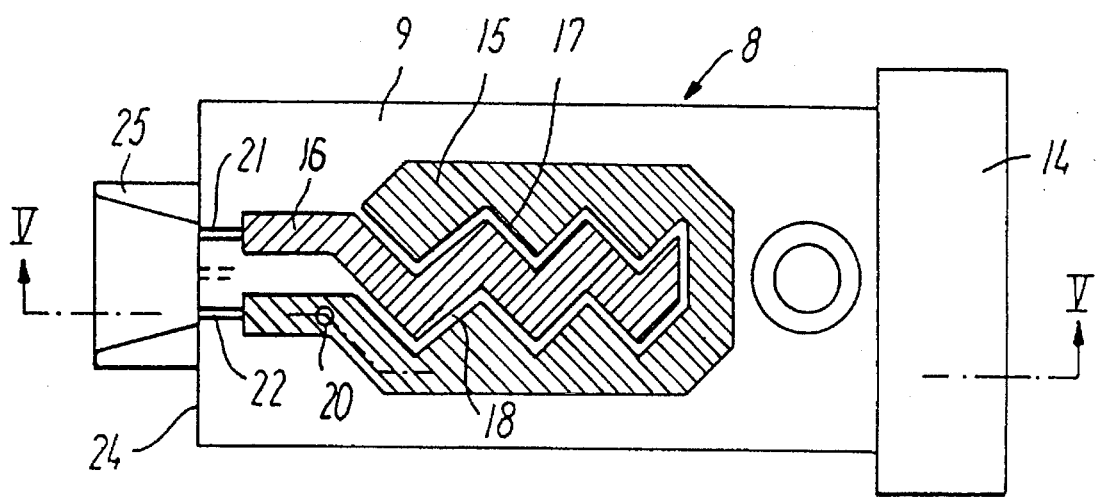
FIGS. 3, 4 and 5 a first embodiment of the sensing element for the rain sensor according to the invention, viewed from above, from below, and in a sectional view along the axis IV—IV in FIG. 2, respectively.
Figure 4:
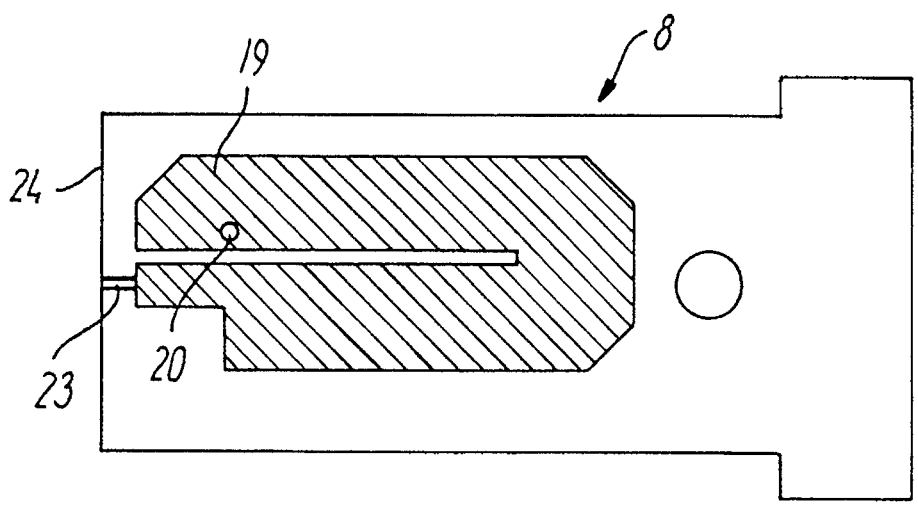
Figure 5:
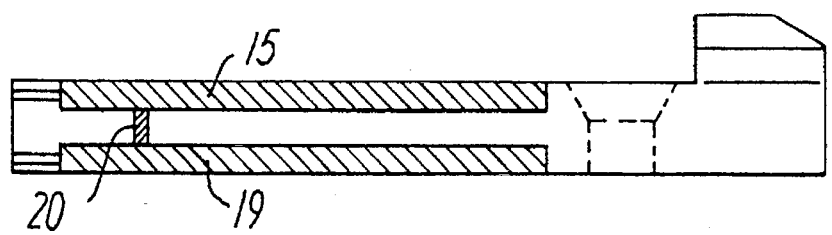

In the embodiment shown in FIGS. 3–5 two electrodes 15 and 16 are mounted on the top side 9 of the holder 8 serving as the sensing surface, one electrode 15 being essentially U-shaped, while the other electrode 16 is positioned in the space between the legs of the U-shaped electrode 15. In order to increase the length of the opposing edges 17 and 18 of the electrodes 15 and 16, respectively, the edges are saw-tooth shaped, and the electrodes 15 and 16 are mounted on the sensor surface 9 such that the distance between them is less than the size of a raindrop, said distance being typically 0.4–0.8 mm. The principle of operation of the rain sensor is that raindrops on the sensing surface will cause a significant reduction in the electrical resistance between the electrodes 15 and 16.

As shown in FIG. 4 a heating element 19, serving the purpose of drying the sensor surface after it has become wet, is mounted onto the bottom side of the holder 8, the heating element being electrically connected to the U-shaped electrode 15 through a transverse connector 20.

In the the shown embodiment the electrodes 15 and 16 as well as the heating element 19 are designed as inserts in the two sides of the holder by molding an electrically conducting thermoplastic polymer into appropriately shaped excavated recesses and/or grooves in the holder 8. The electrodes and the heating element may be made from any suitable thermoplastic polymer, for instance polypropylene or polycarbonate which has been made electrically conducting by the addition of graphite.

According to the invention a simple method for molding the electrodes 15 and 16 as well as the heating element 19 is accomplished by allowing the electrical connectors 21 and 22 leading to the electrodes 15 and 16, as well as the similar electrical lead 23 to the heating element 19, all to connect to a common surface 24 on the side of the holder 8, for instance as shown by the side 24 of the holder 8, the side 24 being situated opposite to the top section 14. The electrodes 15 and 16, as well as the heating element 19 with their adjoining electrical supply line sections 21–23, may thus in a manufacturing process be produced by molding of the electrically conducting thermoplastic polymer.

Exterior electrical supply lines to be connected to the electrical wires 5 in FIG. 1 may be installed in the electrical lead sections 21–23 in a known manner either by melting them into the electrically conducting thermoplastic polymer or by placing them as cover in the plastic during the casting of the electrodes and the heating element.

The illustrated saw-tooth shape of the electrodes 15 and 16 permits the sensor surface to be relatively small while assuring a good and close connection between the electrically conducting parts and the surrounding electrically insulating plastic such that there is no risk of cracks developing on the interface between the two plastics.

A precondition for the embodiment shown in FIGS. 3–5 is that the electrodes 15 and 16 are produced by molding of a plastic into the body of the holder 8. To protect the electrically conducting polymer of the electrodes against destruction due to the effects of the weather a protective electrode coating, not illustrated, containing for instance graphite, may be applied to the plane horizontal electrode surfaces 15 and 16. Such a coating may be applied by a printing process.

Figure 6:
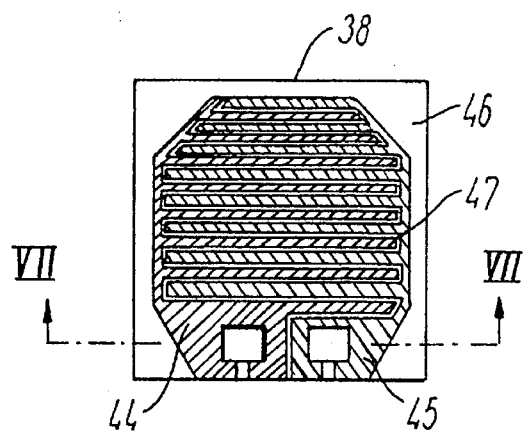
FIGS. 6 and 7 a preferred embodiment of the sensing element viewed from above and in a sectional view cut along the axis VII—VII in FIG. 6.
Figure 7:
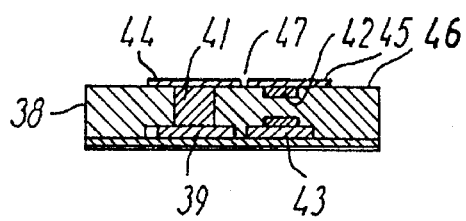

In FIGS. 6 and 7 a preferred embodiment is shown in which a heating element 39, as well as electrical supply lines 41–43 to the heating element and the electrodes, like the embodiment in FIGS. 3–5 is produced by molding of an electrically conducting thermoplastic into the body of the holder 38, the holder 38 having been made from an electrically insulating thermoplastic.

However, the electrode parts functioning as sensing elements are here solely made from printed-on coatings of a weather resistant electrically conducting material, for instance containing graphite. These coatings 44 and 45, which may be applied by a printing process, may—as shown—cover most of the area of the sensing surface 46, preferably at least 70% of this area, being separated only by a linearly shaped uncoated part 47 on the body of the holder 38 proceeding in relatively closely spaced bends across most of the area—preferably at least 80%—of the electrode coatings 44 and 45.

Thereby, an improved utilization of the total area of sensing surface is achieved and as a consequence the sensitivity of the rain sensor is optimized.

Like in the embodiment of FIGS. 3–5 one of the electrical leads 41 is common to the heating element 39 and one of the electrode coatings 44.

However, the electrodes and the heating element may certainly also be designed differently from what is shown and described above and may furthermore be made from other materials such as, for instance, a metal coating either evaporated onto the surface or applied by some other method, although the embodiment consisting of an electrically conducting thermoplastic polymer is preferred. It may furthermore be possible to design a rain sensor without a separate heating element, as one of the electrodes may be utilized as a heating element generating the thermal power required to dry the sensing surface.

Figure 8:
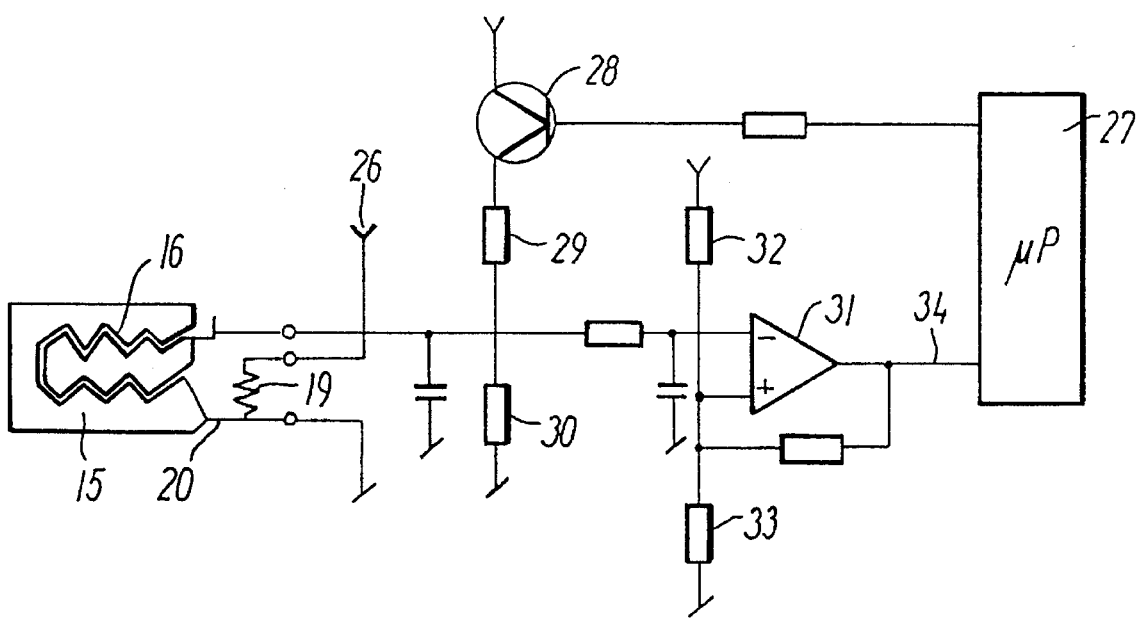
FIG. 8 an example of an electric sensing circuit.

An example of an electric sensing circuit is shown in FIG. 8, in which the heating element 19 is connected to a DC voltage generator 26, which may be controlled in such a manner as to intermittently activate the heating element, such that it is connected only when the drying of a wet sensing surface is required, and where the control of the heating element in addition may be a function of the outside temperature. With the sensing element constructed as described above it has been possible to achieve drying times of less than 5 minutes at an outside temperature of 20° C. through a relatively modest power consumption of approximately 300 mW, which must be considered sufficient for practical purposes.

The sensing circuit is connected to a microprocessor 27, which may be a part of the control circuit 5 in FIG. 1 serving the purpose of controlling the opening and shutting functions of the window in a known fashion. In the shown embodiment of the sensing circuit the microprocessor 27 sends out a short voltage pulse at time intervals of for instance 1,5 seconds, whereby a transistor 28 conducts. Thus voltage division is established between the resistors 29 and 30, whereby the electrode 16 receives a voltage pulse of about 3V. The same voltage pulse is lead to the negative terminal of a comparator 31, realized as a differential amplifier with positive feedback, while a reference signal from the voltage divider established by the resistances 32 and 33 is fed to the positive terminal of the comparator such that a normal response to the transmitted voltage pulse will be a zero signal at an input terminal 34 of the microprocessor 27.

When the presence of raindrops causes a reduced electrical resistance between the electrodes 15 and 16 and thereby a reduction in the potential between the same electrodes an active sensing signal is sent from the comparator 31 to the microprocessor 27, the latter being programmed such that it initiates the closing function for the window frame 2.

The electric sensing circuit may be designed differently from what is shown and described here just as the sensing function need not to be based on a change in the electrical resistance between two electrodes, but may instead be designed as a capacitance sensor where the presence of raindrops results in a change of the dielectric constant in the capacitive element created by the electrodes.

We claim:

1. An electric rain sensor for mounting on the outside of the main frame (1) or on another stationary member of an openable window (1,2) of the type where opening and closing may be carried out by means of an electrical maneuvering device (3), said rain sensor comprising a sensing element (4) with two electrodes (15,16; 44,45) opposite one another in or on a substantially plane sensing surface (9,46) of an insulating holder (8,38), the distance between the electrodes (15,16; 44,45) being less than the size of a raindrop, means for applying a voltage between the electrodes (15,16; 44,45) and an electrical circuit connected to the electrodes for detecting a change in an electrical quantity caused by the presence of raindrops, a heating element (19,39) being mounted on the holder (8,38) for drying of the sensing surface (9,46), and the holder (8,38) being produced by molding of an electrically insulating thermoplastic, characterized in that the heating element (19,39), and supply lines (21–23; 41–43) therefor and for the electrodes (15,16; 44,45), are manufactured as inserts of the holder (8,38) by molding in an electrically conducting thermoplastic polymer into excavated recesses and/or grooves in the holder (8,38).

2. An electric rain sensor according to claim 1, characterized in that the electrodes are manufactured as molded inserts having the electrode surfaces located essentially in the plane of the sensing surface, and that one of the electrodes (15) being essentially U-shaped with one leg connected to a common side surface (24) while the other electrode (16) is positioned in the space between the legs of the U-shaped electrode (15).

3. An electric rain sensor according to claim 2, characterized in that opposing edges (17, 18) of the electrodes (15, 16) are saw-tooth shaped.

4. An electric rain sensor according to claim 1, characterized in that the electrodes include protective electrode coatings made from a weather resistant electrically conducting material on the sensing surface.

5. An electric rain sensor according to claim 4, characterized in that said weather resistant electrically conducting material is a material containing graphite.

6. An electric rain sensor according to claim 4, characterized in that the electrode coatings (44,45) cover most of the area of the sensing surface (46), and are separated by a lineshaped uncoated part (47) of the sensing surface, proceeding in relatively closely spaced bends over most of i the area of the electrode coatings.

7. An electric rain sensor according to claim 6, characterized in that the electrode coatings (44,45) cover at least 70% of the area of the sensing surface.

8. An electric rain sensor according to claim 6, characterized in that said lineshaped uncoated part (47) extends across at least 80% of the area of the electrode coatings.

9. An electric rain sensor according to claim 1, characterized in that the heating element (19,39) is molded into a side surface of the holder (8) opposite to the sensing surface (9) and is connected to one electrode (15,44) through a transverse duct (20) in the holder (8).

10. An electric rain sensor according to claim 1, characterized in that the supply lines of the electrodes and the heating element are all connected to a common side surface (24) of the holder (8).

11. A method of manufacturing a sensor element for an electric rain sensor for mounting on the outside of the main frame (1) or on another stationary member of an openable window (1,2) of the type where opening and closing may be carried out by means of an electrical maneuvering device (3), said rain sensor comprising a sensing element (4) with two electrodes (15,16; 44,45) opposite one another in or on a substantially plane sensing surface (9,46) of an insulating holder (8,38), the distance between the electrodes (15,16; 44,45) being less than the size of a raindrop, means for applying a voltage between the electrodes (15,16; 44,45) and an electrical circuit connected to the electrodes for detecting a change in an electrical quantity caused by the presence of raindrops, a heating element (19,39) being mounted on the holder (8,38) for drying of the sensing surface (9,46), and the holder (8,38) being produced by molding of an electrically insulating thermoplastic, characterized in that the heating element (19,39), and supply lines (21–23; 41–43) therefor and for the electrodes (15,16; 44,45), are manufactured as inserts of the holder (8,38) by molding in an electrically conducting thermoplastic polymer into excavated recesses and/or grooves in the holder (8,38), the method characterized in that the electrodes (15,16; 44,45), the heating element (19,39), and the adjoining supply lines (21–23; 41–43), all being designed as integrated molded parts of the rain sensor, are produced in one operation by molding of the electrically conducting thermoplastic polymer into appropriately shaped excavated recesses and/or grooves in the holder (8,38).

12. A method for manufacturing a sensor element for an electric rain sensor as claimed in claim 11 characterized in that electrode coatings are applied to the sensing surface through a pressing process with subsequent curing by baking.

* * * * *

UNITED STATES PATENT AND TRADEMARK OFFICE
CERTIFICATE OF CORRECTION

PATENT NO. : 5,533,391

DATED : July 9, 1996

INVENTOR(S) : Claus B. Brade et al.

It is certified that error appears in the above-identified patent and that said Letters Patent is hereby corrected as shown below:

Title page , item [22] "Jul. 9, 1993" should read --Jul. 2, 1993--

Signed and Sealed this

Thirteenth Day of May, 1997

*Attest:*

BRUCE LEHMAN

*Attesting Officer*

*Commissioner of Patents and Trademarks*